US012397133B2

(12) United States Patent
Cabiri

(10) Patent No.: US 12,397,133 B2
(45) Date of Patent: Aug. 26, 2025

(54) STEERING TOOL

(71) Applicant: Bendit Technologies Ltd., Petach Tikva (IL)

(72) Inventor: Oz Cabiri, Hod HaSharon (IL)

(73) Assignee: Bendit Technologies Ltd., Petach Tikva (IL)

( * ) Notice: Subject to any disclaimer, the term of this patent is extended or adjusted under 35 U.S.C. 154(b) by 0 days.

(21) Appl. No.: 18/459,441

(22) Filed: Sep. 1, 2023

(65) Prior Publication Data

US 2023/0405276 A1 Dec. 21, 2023

Related U.S. Application Data

(63) Continuation of application No. 16/884,173, filed on May 27, 2020, now abandoned, which is a continuation of application No. 14/044,886, filed on Oct. 3, 2013, now abandoned.

(51) Int. Cl.
*A61M 25/01* (2006.01)
*A61B 17/00* (2006.01)
*A61M 25/06* (2006.01)
*A61M 25/09* (2006.01)

(52) U.S. Cl.
CPC ... *A61M 25/0138* (2013.01); *A61B 17/00234* (2013.01); *A61M 25/0141* (2013.01); *A61M 25/06* (2013.01); *A61B 2017/00305* (2013.01); *A61B 2017/00309* (2013.01); *A61M 25/0102* (2013.01); *A61M 25/0136* (2013.01); *A61M 25/09* (2013.01)

(58) Field of Classification Search
CPC ............. A61M 25/0138; A61M 25/06; A61M 25/0102; A61M 25/0136; A61M 25/09; A61B 17/00234; A61B 2017/00309
See application file for complete search history.

(56) References Cited

U.S. PATENT DOCUMENTS

| | | | |
|---|---|---|---|
| 3,802,440 A * | 4/1974 | Salem | A61M 16/0429 138/120 |
| 5,106,381 A * | 4/1992 | Chikama | A61M 25/0138 604/528 |
| 2009/0281498 A1 * | 11/2009 | Acosta | A61B 17/3421 604/164.01 |
| 2012/0277730 A1 * | 11/2012 | Salahieh | A61M 25/0144 604/528 |
| 2013/0304034 A1 * | 11/2013 | Cabiri | A61M 25/0138 604/528 |

* cited by examiner

*Primary Examiner* — May A Abouelela
*Assistant Examiner* — Yasmeen S Warsi
(74) *Attorney, Agent, or Firm* — Dekel Patent Ltd.; David Klein

(57) ABSTRACT

A steering tool includes an internal tube disposed inside an external tube. The internal and external tubes are arranged for longitudinal axial movement relative to one another. A distal end of the internal tube is fixedly joined to a distal end of the external tube. At least one of the internal and external tubes is slotted near the distal end thereof, and the longitudinal axial movement causes bending of the distal ends of the tubes.

10 Claims, 4 Drawing Sheets

STEERING TOOL

CROSS-REFERENCE TO PRIOR APPLICATIONS

This application is a continuation of and claims priority from U.S. patent application Ser. No. 16/884,173, filed 27 May 2020, which a continuation of and claims priority from U.S. patent application Ser. No. 14/044,886, filed 3 Oct. 2013.

FIELD OF THE INVENTION

The present invention generally relates to a steering tool for steering medical devices through body lumens.

BACKGROUND OF THE INVENTION

PCT Patent Application PCT/US2013/040691, to the present inventor, describes a steering tool for steering medical devices through body lumens. The steering tool has an internal tube disposed inside an external tube. The internal and external tubes are arranged for longitudinal axial movement relative to one another. The distal end of the internal tube is fixedly joined to the distal end of the external tube. One or both of the internal and external tubes is slotted near the distal end thereof. The longitudinal axial movement causes bending of the distal ends of the tubes. One or both of the internal and external tubes are slotted near the distal ends thereof. The steering tool provides a distal tip which combines steerability, flexibility and torqueability. The tool eliminates the need for pull/push wires.

Some of the advantages of that steering tool include reduced cross section, circular cross section in each direction for uniform stability of bending in different directions (towards two or more sides), very thin wall thickness, and applicability to very small tubes (e.g., diameters of 0.2-3 mm). The steering tool also works well with larger tubes. The steering tool simplifies production and reduces the number of parts for any steerable endoscope in medical and industrial fields.

SUMMARY OF THE INVENTION

The present invention seeks to provide further improvements to the steering tool for steering medical devices through body lumens, as is described more in detail hereinbelow.

There is thus provided in accordance with an embodiment of the present invention a steering tool including an internal tube disposed inside an external tube, the internal and external tubes being arranged for longitudinal axial movement relative to one another, wherein a distal end of the internal tube is fixedly joined to a distal end of the external tube, and at least one of the internal and external tubes is slotted near the distal end thereof, and wherein the longitudinal axial movement causes bending of the distal ends of the tubes.

In accordance with an embodiment of the present invention both of the internal and external tubes are slotted near the distal ends thereof.

In accordance with an embodiment of the present invention shapes of the slots change as a parameter of distance from the distal ends of the internal and external tubes.

In accordance with an embodiment of the present invention the internal and external tubes are each formed with one or more alignment holes for correct axial and rotational alignment of the internal and external tubes during joining and assembly.

In accordance with an embodiment of the present invention an alignment pin is inserted in the one or more alignment holes.

In accordance with an embodiment of the present invention an open-ended axial slot is formed in at least one of the internal and external tubes. The axial slot may be open to the most distal slot of the transverse slots.

In accordance with an embodiment of the present invention the transverse slots decrease in length and width with increased distance from the distal ends of the internal and external tubes.

The slots limit the amount of possible tube bending to avoid damage to the tubes. For example, the outer slots protect while pushing and the internal slots protect while pulling the internal tube.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 2:
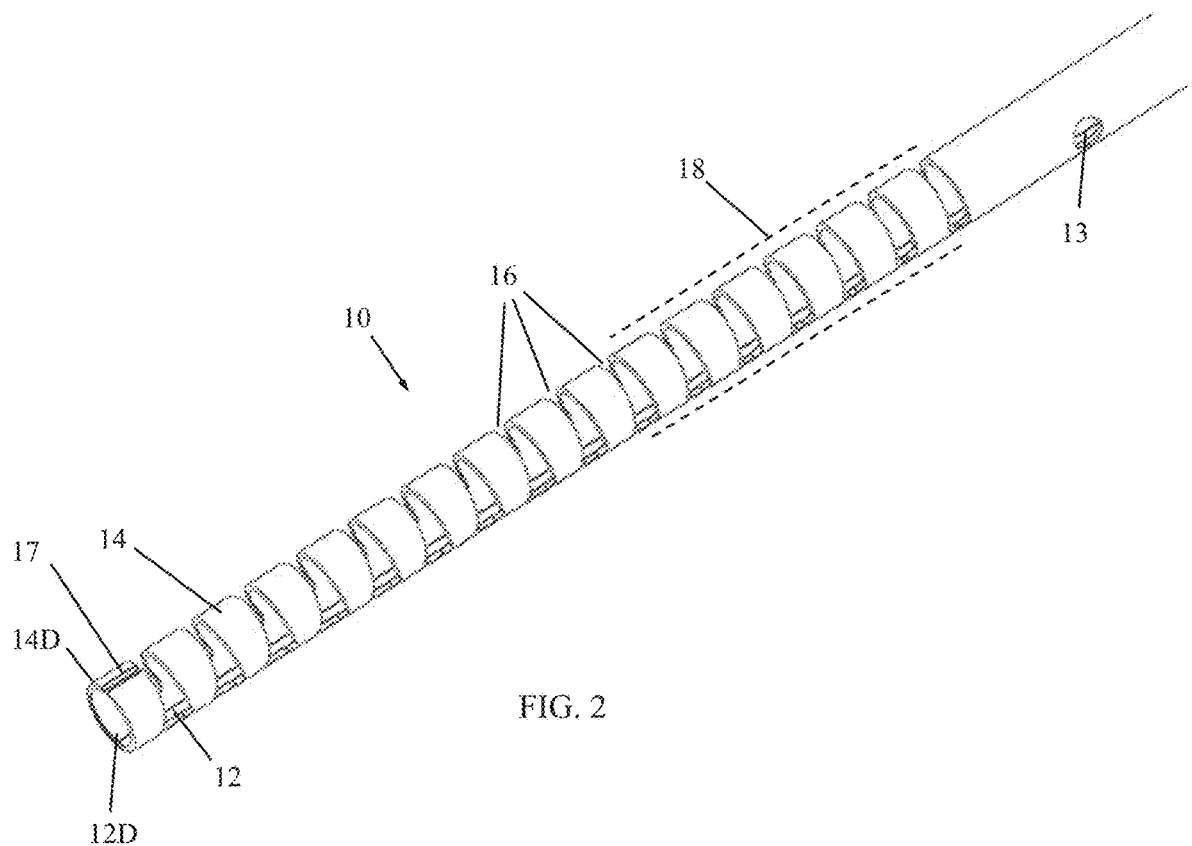
FIG. 2 is a simplified illustration of the steering tool, in accordance with a non-limiting embodiment of the present invention, showing internal and external tubes which are slotted.
Figure 3:
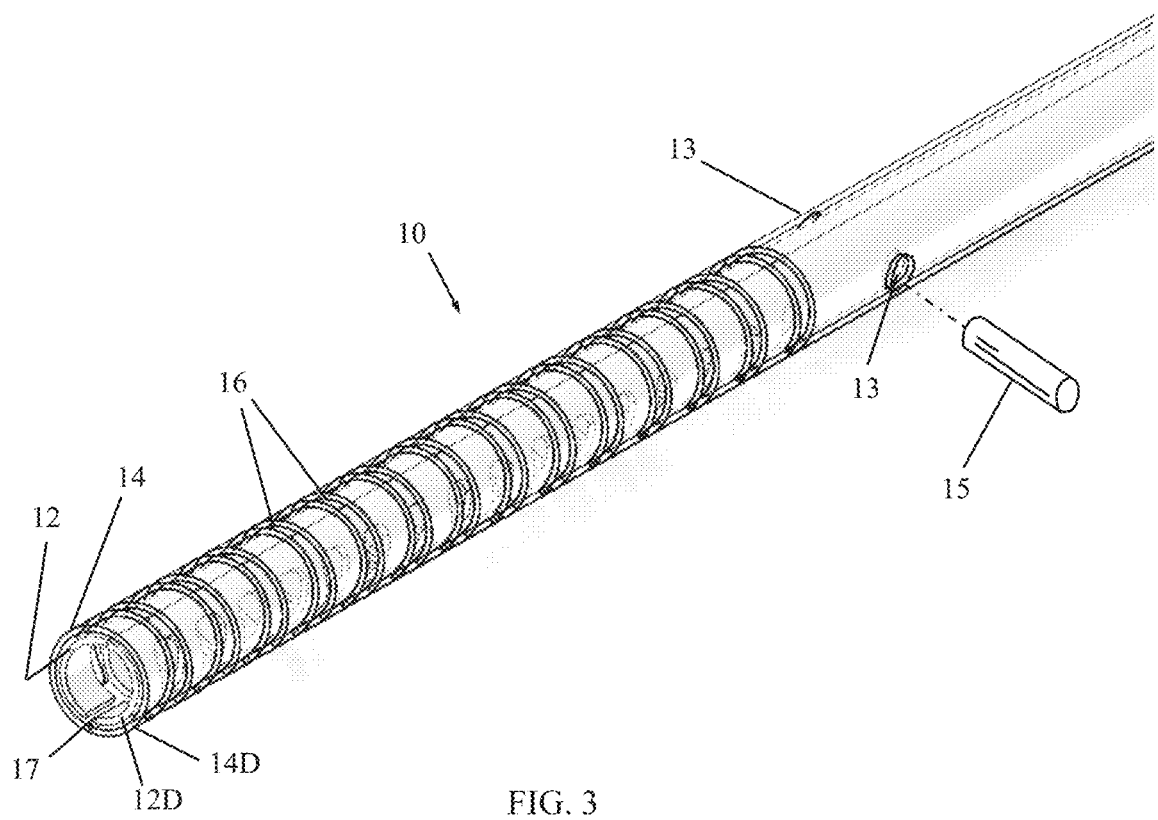
FIG. 3 is a simplified illustration of the steering tool, showing an alignment pin for proper alignment of the tubes during assembly.

Reference is now made to FIGS. 2 and 3, which illustrate a steering tool 10, in accordance with a non-limiting embodiment of the present invention.

Steering tool 10 includes an internal tube 12 disposed inside an external tube 14. A distal end 12D of internal tube 12 is fixedly joined to a distal end 14D of external tube 14. The term "joined" encompasses any method for attaching the materials of the tubes together, such as but not limited to, welding, ultrasonic welding, thermal bonding, adhesive bonding, molding, and others. The internal and external tubes 12 and 14 are arranged for longitudinal axial movement relative to one another (except for their distal ends which are joined together).

In accordance with an embodiment of the present invention, internal tube 12 and external tube 14 are each formed with one or more alignment holes 13 for correct alignment (including axial and rotational alignment about the longitudinal axis) of the tubes during joining and assembly. An alignment pin 15 (FIG. 3) may be inserted in alignment holes 13 to hold the tubes in the proper alignment during joining. The alignment holes 13 may be off-center and/or of two different diameters to ensure that the tubes are not accidentally aligned incorrectly.

The outer diameter of internal tube 12 is smaller than the inner diameter of external tube 14 so they can easily slide relative to each other. This difference in diameter may pose a problem during welding or other types of joining. In accordance with an embodiment of the present invention, in order to achieve good joining (e.g., welding or bonding) between the tubes despite the difference in diameters, an open-ended axial slot 17 is formed in internal tube 12 and/or external tube 14. Slot 17 provides a path for welding, soldering or adhesive material to flow and join the tubes together.

Internal and external tubes 12 and 14 may be made of any suitably flexible, medically safe material, such as but not limited to, stainless steel (e.g., AISI 316), nitinol, cobalt-chromium alloy, nickel-titanium alloy, and others, glass fibers, plastics (e.g., nylon, polypropylene, and many others) or combinations thereof. As will be described further below, the tubes can be used for applications involving light guides, lasers, optic or electrical transfer and other uses, in addition to the mechanical function of bending.

At least one of the internal and external tubes 12 and 14 is slotted with slots 16 near the distal end thereof (e.g., transverse to the longitudinal axis of the tubes; the term transverse encompassing any angle—not just perpendicular—which is not parallel to the longitudinal axis of the tubes). In the preferred embodiment both tubes are slotted, but alternatively only one of the internal and external tubes is slotted and the other may be flexible but not slotted. The longitudinal axial movement causes bending of the distal ends of the tubes (on account of them being joined together), as is known from PCT/US2013/040691. One of the internal and external tubes can be longer than the other (e.g., the internal one is longer for grasping its proximal end for pushing and pulling thereof).

Slots 16 increase the flexibility toward the distal end of the tube or tubes for steerability of the device and controlled manipulation thereof. The amount of flexibility can be controlled by the number of slots, spacing therebetween, shape of the slot, angle subtended by the slot, thickness of the tube, material of the tube, and other factors. Slots 16 may subtend an arc of about 180-270°.

Figure 1:
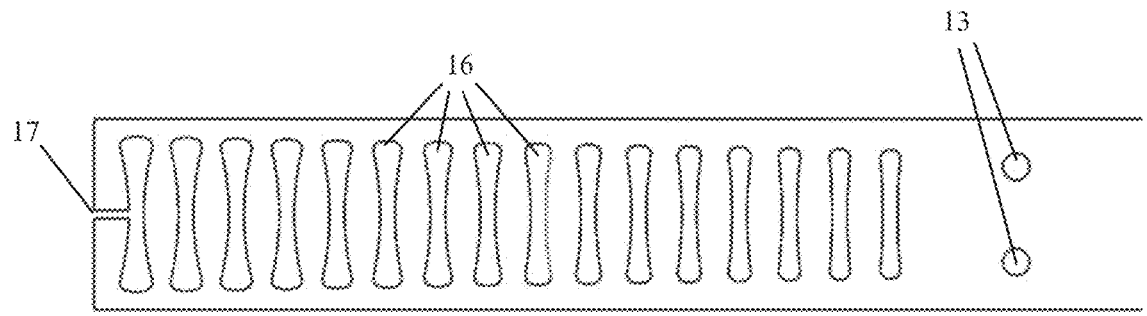
FIG. 1 is a simplified illustration of a steering tool, in accordance with a non-limiting embodiment of the present invention, showing one of the tubes of the steering tool in a spread-out view.

For example, as seen in FIG. 1, the shapes of slots 16 change as a parameter of distance from the distal end. In the illustrated example, the slots decrease in length and width (e.g., asymptotically to a minimum size) with increased distance from the distal end. In this manner, the bending radius remains basically constant at any distance from the distal end and the bending moment increases with increased distance from the distal end. Axial slot 17 may be open to the most distal slot 16.

Figure 4:
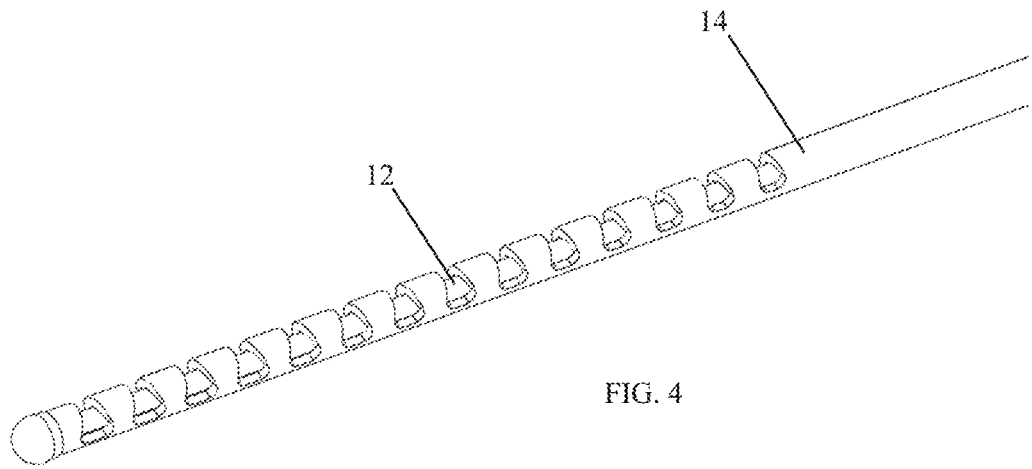
FIG. 4 is a simplified illustration of the steering tool with the internal part being a hollow tube with no slots or a conduit for fluid or wires for energy delivery or optic fiber to transfer optic data or laser.

The steering tool 10 may be covered with a semi-rigid or flexible sheath 18 (shown partially in broken lines in FIG. 2) and used as a catheter or needle. In a more preferred embodiment, shown in FIG. 4, the internal tube 12 is a simple tube or wire with no slots. In the case of a hollow tube, the internal tube 12 can serve as the conduit for delivery of fluids, light, laser, optic, cameras, illumination, electrical energy transfer (e.g., wired connections), and others, in addition to the mechanical function of bending, Thus, the device can be used to deliver fluids to places in a body with high accuracy, such as but not limited to, direct injection of drugs into the brain. For example, tool 10 may be used as a needle to protrude through or into a blood vessel and inject substances directly into the brain, tumor or infected area. The steering tool 10 may be used as a catheter to direct and deliver cooled gas to freeze tumors or other areas. The steering tool 10 may be used as a catheter to guide fiber optic or laser devices for illumination, treatment, ablation or drying or other uses. In another embodiment, the fiber optic can be part of the mechanical steering system, serving as a pull wire inside the internal or external tube. In this manner, a controlled fiber optic with a diameter of 0.3 mm becomes feasible.

In any of the embodiments, the distal edge shape of the internal tube, external tube and/or overall tool may be not only circular, but also shaped as an electrode, needle or other shapes.

Figure 5A:
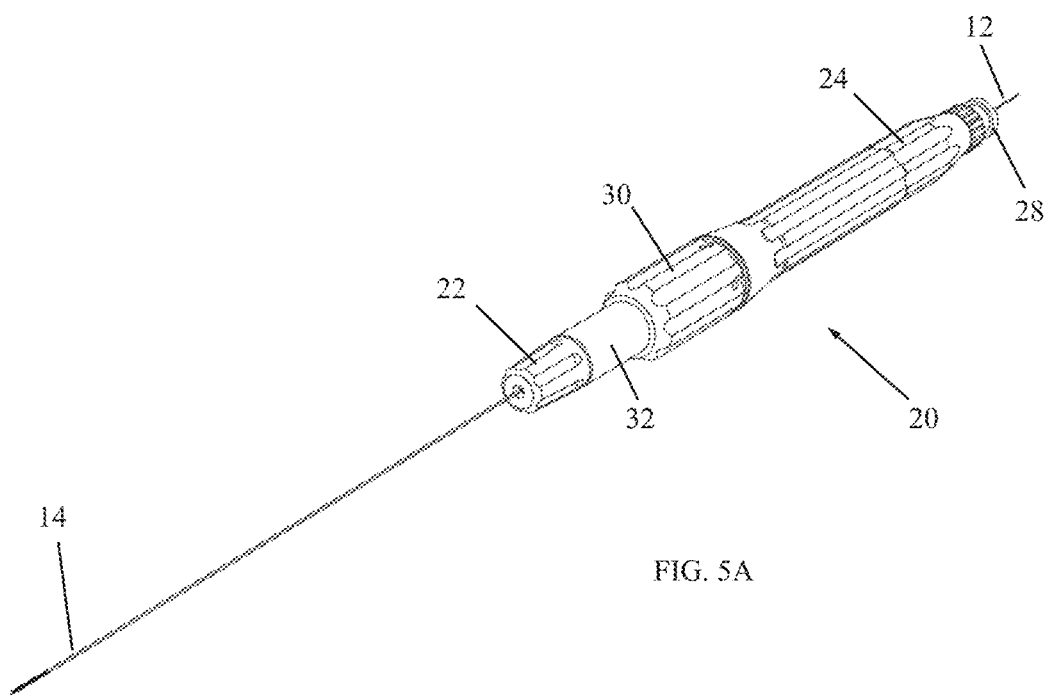
FIGS. 5A and 5B are simplified pictorial and cutaway illustrations, respectively, of a steering tool with a manipulation handle, constructed and operative in accordance with a non-limiting embodiment of the present invention.
Figure 5B:
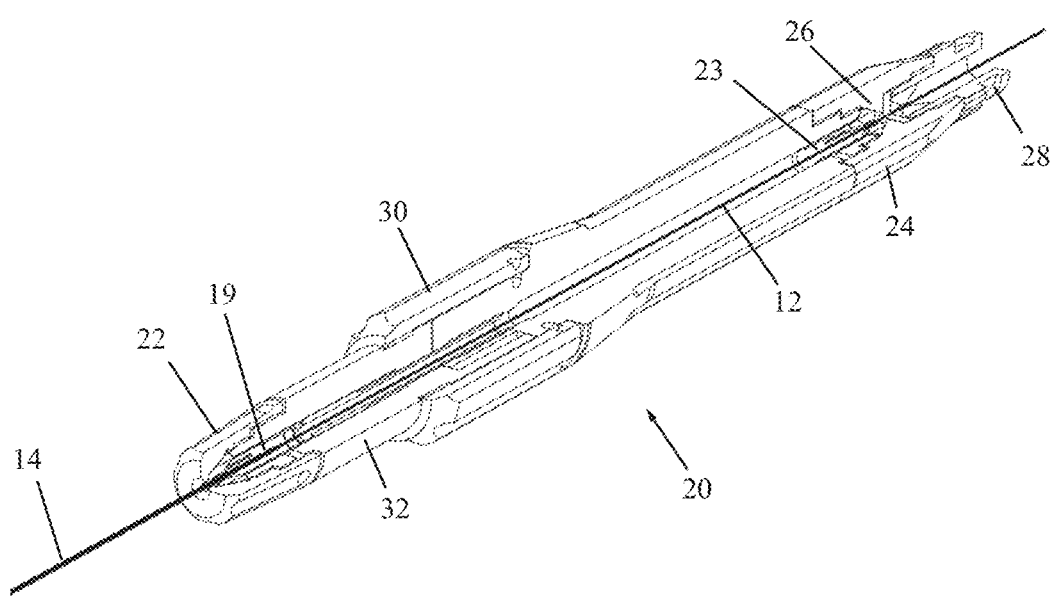

Reference is now made to FIGS. 5A and 5B, which illustrate a steering tool with a manipulation handle 20, constructed and operative in accordance with a non-limiting embodiment of the present invention.

In this steering tool, the proximal end 19 of the external tube 14 is affixed or locked in an external tube holder 22 at the distal end of the handle 20. The internal tube 12 is disposed in external tube 14 as described above. The internal tube 12 extends through the length of handle 20, and a proximal portion 23 of internal tube 12 may be held by a proximal internal tube holder 24. The internal tube holder 24 may include a septum 26 which may be used to seal passage of the internal tube 12 therethrough. The handle 20 may be provided with a proximal fluid connector 28.

The handle 20 is provided with a tube manipulator 30, such as a linear slider, for causing relative axial movement of the internal and external tubes. For example, the tube manipulator 30 may abut against or be connected to a movable portion 32 of handle 20, which is connected to or abuts against the external tube holder 22. By moving tube manipulator 30 distally, the movable portion 32 also moves distally and causes the internal tube 12 to move distally as well, thereby causing bending of the distal tip of the internal and external tubes, as described above. The tube manipulator 30 may abut proximally against a stationary portion of the handle 20 and/or may "click" into a groove formed in the handle, which serves as a proximal stop and locks the tube manipulator 30 in place. The tube manipulator 30 may be released when desired from the locked position and relocked in place. Thus, the steering tool can be used very easily as a guide wire for guiding catheters and other devices.

What is claimed is:

1. A steering tool comprising:
an internal tube disposed inside an external tube, said internal and external tubes being arranged for longitudinal axial movement relative to one another, wherein a distal end of said internal tube is fixedly joined to a distal end of said external tube, and at least one of said internal and external tubes is formed with transverse slots near the distal end thereof, and wherein the longitudinal axial movement causes bending of the distal ends of said internal and external tubes;

and wherein shapes of said transverse slots change as a parameter of distance from the distal ends of said internal and external tubes; and wherein said internal tube is coupled to an internal tube holder that comprises a septum that seals passage of said internal tube therethrough, said septum comprises a radially outward portion secured to an inner surface of said internal tube holder and an inner aperture through which said internal tube passes therethrough; and wherein a proximal end of said external tube is affixed or locked in an external tube holder at a distal end of a handle and said internal tube extends through said handle, a proximal portion of said internal tube being held by a proximal internal tube holder, and wherein said handle comprises a tube manipulator operative to cause relative axial movement of said internal and external tubes, and wherein said tube manipulator is arranged to abut against or be connected to a movable portion of said handle, said movable portion being connected to or abutting against said external tube holder, and wherein distal movement of said tube manipulator causes said movable portion to move distally and cause said internal tube to move distally to cause bending of distal tips of said internal and said external tubes, and wherein said tube manipulator is arranged to click into a groove formed in said handle to lock said tube manipulator in place.

2. The steering tool according to claim 1, wherein said internal and external tubes are each formed with one or more alignment holes for correct axial and rotational alignment of said internal and external tubes during joining and assembly.

3. The steering tool according to claim 2, further comprising an alignment pin inserted in said one or more alignment holes.

4. The steering tool according to claim 1, further comprising an open-ended axial slot formed in at least one of said internal and external tubes.

5. The steering tool according to claim 4, wherein said open-ended axial slot is open to a most distal slot of the transverse slots.

6. The steering tool according to claim 1, wherein said transverse slots decrease in length and width with increased distance from the distal ends of said internal and external tubes.

7. The steering tool according to claim 6, wherein said transverse slots decrease in length and width asymptotically to a minimum size.

8. The steering tool according to claim 1, wherein said steering tool is covered with a semi-rigid or flexible sheath.

9. The steering tool according to claim 1, wherein both of said internal and external tubes are slotted near their distal ends.

10. The steering tool according to claim 1, wherein said radially outward portion comprises steps located at different radially outward positions, each of said steps extending along a longitudinal axis of said internal tube holder.

* * * * *